(12) United States Patent
Wiemer et al.

(10) Patent No.: US 11,926,641 B2
(45) Date of Patent: Mar. 12, 2024

(54) PHOSPHONAMIDATE BUTYROPHILIN LIGANDS

(71) Applicants: UNIVERSITY OF IOWA RESEARCH FOUNDATION, Iowa City, IA (US); UNIVERSITY OF CONNECTICUT, Farmington, CT (US)

(72) Inventors: David F. Wiemer, Iowa City, IA (US); Andrew J. Wiemer, Vernon, CT (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 795 days.

(21) Appl. No.: 16/981,884

(22) PCT Filed: Mar. 15, 2019

(86) PCT No.: PCT/US2019/022529
§ 371 (c)(1),
(2) Date: Sep. 17, 2020

(87) PCT Pub. No.: WO2019/182904
PCT Pub. Date: Sep. 26, 2019

(65) Prior Publication Data
US 2021/0115074 A1 Apr. 22, 2021

Related U.S. Application Data

(60) Provisional application No. 62/645,020, filed on Mar. 19, 2018.

(51) Int. Cl.
*C07F 9/44* (2006.01)
*A61K 45/06* (2006.01)

(52) U.S. Cl.
CPC ............ *C07F 9/4465* (2013.01); *A61K 45/06* (2013.01)

(58) Field of Classification Search
CPC .................................................. C07F 9/4465
See application file for complete search history.

(56) References Cited

U.S. PATENT DOCUMENTS

| 2008/0318227 A1 | 12/2008 | Bacher et al. |
| 2009/0069268 A1 | 3/2009 | Shepard et al. |

FOREIGN PATENT DOCUMENTS

| WO | 2003009855 A2 | 2/2003 |
| WO | 2008059052 A1 | 5/2008 |
| WO | 2008146167 A2 | 12/2008 |
| WO | 2010049438 A2 | 5/2010 |

OTHER PUBLICATIONS

Cancer and Metastasis Reviews (1998), 17(1), 91-106.*
Science (1999), vol. 286, 531-537.*
Cancer [online], [retrieved on Jul. 24, 2023]. Retrieved from the internet, URL https://medlineplus.gov/cancer.html>.*
Boedec, A , et al., "Synthesis and biological activity of phosphonate analogues and geometric isomers of the highly potent phosphoantigen (E)-1-hydroxy-2-methylbut-2-enyl 4-diphosphate", J Med Chem 51(6), 1747-1754 (2008).
Foust, B , et al., "Mixed Aryl Phosphonate Prodrugs of a Butyrophilin Ligand", ACS Med. Chem. Lett. 8, 914-918 (2017).
Harmon, N , et al., "Incorporation of a FRET pair within a phosphonate diester", Bioorganic Chemistry 114, 105048, 11 pages (2021).
Harmon, N , et al., "Synthesis and Biological Activity of Coumarin-Containing Prodrugs of a Butyrophilin Ligand", Abstracts of Papers, 255th ACS National Meeting & Exposition, New Orleans, LA, United States, Mar. 18-22, 2018 (2018), MEDI-372. Publisher: (American Chemical Society, Washington, D. C) CODEN:69WAWX.
Hsiao, C , et al., "A power law function describes the time- and dose-dependency of Vγ9Vδ2 T cell activation by phosphoantigens", Biochemical Pharmacology 158, 298-304 (2018).
Hsiao, C. , et al., "Synthesis of a Phosphoantigen Prodrug that Potently Activates V9V2 T-Lymphocytes", Chemistry & Biology, vol. 21, 945-954 (2014).
Entini, N , et al., "Phosphonamidate Prodrugs of a Butyrophilin Ligand Display Plasma Stability and Potent Vγ9 Vδ2 T Cell Stimulation", J Med Chem 61, 8658-8669 (2018).
Nguyen, K. , et al., "The butyrophilin 3A1 intracellular domain undergoes a conformational change involving the juxtamembrane region", FASEB J 31, 4697-4706 (2017).
Patent Cooperation Treaty , International Searching Authority, Search Report and Written Opinion for PCT/US2019/022529, 9 pages dated May 13, 2019.
Shippy, R , et al., "Phosphinophosphonates and Their Tris-pivaloyloxymethyl Prodrugs Reveal a Negatively Cooperative Butyrophilin Activation Mechanism", J Med Chem 60(6), 2373-2382 (2017).
Wiemer, D , et al., "Opportunities and challenges in development of phosphoantigens as Vγ9Vδ2 T cell agonists", Biochem Pharmacol 89(3), 301-312 (2014).
Wiemer, A , et al., "Prodrugs of phosphonates and phosphates: crossing the membrane barrier", Top Curr Chem 360, 115-160 (2015).

* cited by examiner

*Primary Examiner* — Shawquia Jackson
(74) *Attorney, Agent, or Firm* — Viksnins Harris Padys Malen LLP

(57) ABSTRACT

The invention provides a compound of formula I: or a salt thereof, wherein $R^1$-$R^4$ have any of the values described in the specification, as well as compositions comprising a compound of formula I. The compounds are useful in immunotherapy as a potential treatment, or co-treatment, for cancer or infectious diseases.

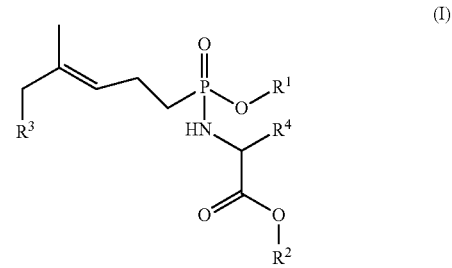

(I)

18 Claims, 9 Drawing Sheets

100 R$^1$ = R$^2$ = Na
101 R$^1$ = R$^2$ = CH$_3$
102 R$^1$ = phenyl; R$^2$ = POM
103 R$^1$ = 1-naphthyl; R$^2$ = POM
104 R$^1$ = POM; R$^2$ = POM

PHOSPHONAMIDATE BUTYROPHILIN LIGANDS

PRIORITY APPLICATION

This application claims priority to U.S. Provisional Application No. 62/645,020 that was filed on Mar. 19, 2018. The entire content of the application referenced above is hereby incorporated by reference herein.

GOVERNMENT FUNDING

This invention was made with government support under CA186935 awarded by the National Institutes of Health. The government has certain rights in this invention.

BACKGROUND

There are a wide variety of anti-cancer drugs currently on the market. However, many forms of cancer still have a low cure rate especially with metastatic disease.

Binding of small phosphorus-containing compounds to BTN3A1 induces a conformational change in the intracellular domain which subsequently leads to activation of the Vγ9Vδ2 cell receptor through unknown mechanisms (Wiemer D. F.; Wiemer, A. J. *Biochemical Pharmacology*, 2014, 89, 301-312; Hsiao C, et al., *Chemistry and Biology*, 2014, 21, 945-954; and Nguyen, K., et al., FASEB J. 2017, 31, 4697-4706). Due to its intrinsic connection to T cell proliferation, BTN3A1 could be an innovative target to stimulate the immune response to infectious diseases and cancer.

One butyrophilin ligand has previously reached clinical trials, a compound called BrHPP, which is an analog of the natural butyrophilin ligand HMBPP. BrHPP and HMBPP are not stable in plasma, which limits dosing.

Currently there is a need for anti-cancer agents (e.g. butyrophilin ligands) with improved properties (e.g., plasma stability).

SUMMARY

In one embodiment the invention provides a series of compounds that trigger activation of human gamma delta T cells through binding to the protein butyrophilin 3A1. In contrast to prior compounds, the compounds are resistant to degradation by plasma esterases, resulting in enhanced plasma stability. The compounds of the invention could be used in immunotherapy as a potential treatment, or co-treatment, for cancer or infectious diseases.

Accordingly, in one embodiment the invention provides a compound of the invention, which is a compound of formula I:

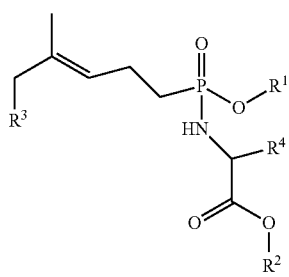
(I)

or a salt thereof, wherein:

$R^1$ is aryl, 5-6 membered heteroaryl, aryl($C_1$-$C_6$)alkyl, or (5-6 membered heteroaryl)($C_1$-$C_6$)alkyl, wherein any aryl, 5-6 membered heteroaryl, aryl($C_1$-$C_6$)alkyl, or (5-6 membered heteroaryl)($C_1$-$C_6$)alkyl is optionally substituted with one or more groups $R^x$ independently selected from the group consisting of hydroxyl, halo, nitro, cyano, carboxy, $NR^aR^b$, ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkylthio, and ($C_2$-$C_6$)alkanoyloxy, wherein any ($C_1$-$C_6$)alkyl and ($C_1$-$C_6$)alkoxy of $R^x$ is optionally substituted with one or more groups independently selected from halo;

$R^2$ is ($C_1$-$C_6$)alkyl that is optionally substituted with one or more groups independently selected from the group consisting of hydroxy, halo, nitro, cyano, carboxy, $NR^cR^d$, ($C_1$-$C_6$)alkoxy, ($C_1$-$C_6$)alkanoyl, ($C_1$-$C_6$)alkoxycarbonyl, ($C_1$-$C_6$)alkylthio, and ($C_2$-$C_6$)alkanoyloxy;

$R^3$ is oxo (=O) or hydroxy;

$R^4$ is the side-chain of a natural amino acid;

each $R^a$ and $R^b$ is independently selected from the group consisting of H, ($C_1$-$C_6$)alkyl, ($C_3$-$C_6$)cycloalkyl, and ($C_3$-$C_6$)cycloalkyl($C_1$-$C_6$)alkyl; or $R^a$ and $R^b$ together with the nitrogen to which they are attached form a aziridino, azetidino, morpholino, piperazino, pyrrolidino or piperidino; and each $R^c$ and $R^d$ is independently selected from the group consisting of H, ($C_1$-$C_6$)alkyl, ($C_3$-$C_6$)cycloalkyl, and ($C_3$-$C_6$)cycloalkyl($C_1$-$C_6$)alkyl; or $R^c$ and $R^d$ together with the nitrogen to which they are attached form a aziridino, azetidino, morpholino, piperazino, pyrrolidino or piperidino.

In one embodiment the invention provides a pharmaceutical composition comprising a compound of formula I, or a pharmaceutically acceptable salt thereof, and a pharmaceutically acceptable excipient.

In one embodiment the invention provides a method for stimulating an immune response in an animal (e.g., a mammal such as a human) comprising administering a compound of formula I as described in any one of claims 1-7, or a pharmaceutically acceptable salt thereof, to the animal.

In one embodiment the invention provides a method for treating an infectious disease in an animal (e.g., a mammal such as a human) comprising administering a compound of formula I or a pharmaceutically acceptable salt thereof, to the animal.

In one embodiment the invention provides a method for treating cancer in an animal (e.g., a mammal such as a human) comprising administering a compound of formula I or a pharmaceutically acceptable salt thereof, to the animal.

In one embodiment the invention provides a method for triggering the activation of gamma delta T cells in a human comprising administering a compound of formula I or a pharmaceutically acceptable salt thereof, to the human.

In one embodiment the invention provides a compound of formula I or a pharmaceutically acceptable salt thereof, for use in medical therapy.

In one embodiment the invention provides a compound of formula I or a pharmaceutically acceptable salt thereof, for the prophylactic or therapeutic treatment of cancer or an infectious disease.

In one embodiment the invention provides a compound of formula I or a pharmaceutically acceptable salt thereof, for the prophylactic or therapeutic treatment of a disease wherein activation of gamma delta T cells in a human is indicated.

In one embodiment the invention provides the use of a compound of formula I or a pharmaceutically acceptable salt thereof, to prepare a medicament for stimulating an immune response.

In one embodiment the invention provides the use of a compound of formula I or a pharmaceutically acceptable salt thereof, to prepare a medicament for treating cancer or an infectious disease.

In one embodiment the invention provides the use of a compound of formula I or a pharmaceutically acceptable salt thereof, to prepare a medicament for treating a disease wherein activation of gamma delta T cells in a human is indicated.

In one embodiment the invention provides the use of a compound of formula I or a pharmaceutically acceptable salt thereof, to prepare cells for treating a disease wherein cell based immunotherapy with gamma delta T cells in a human is indicated.

DETAILED DESCRIPTION

Figure 1:
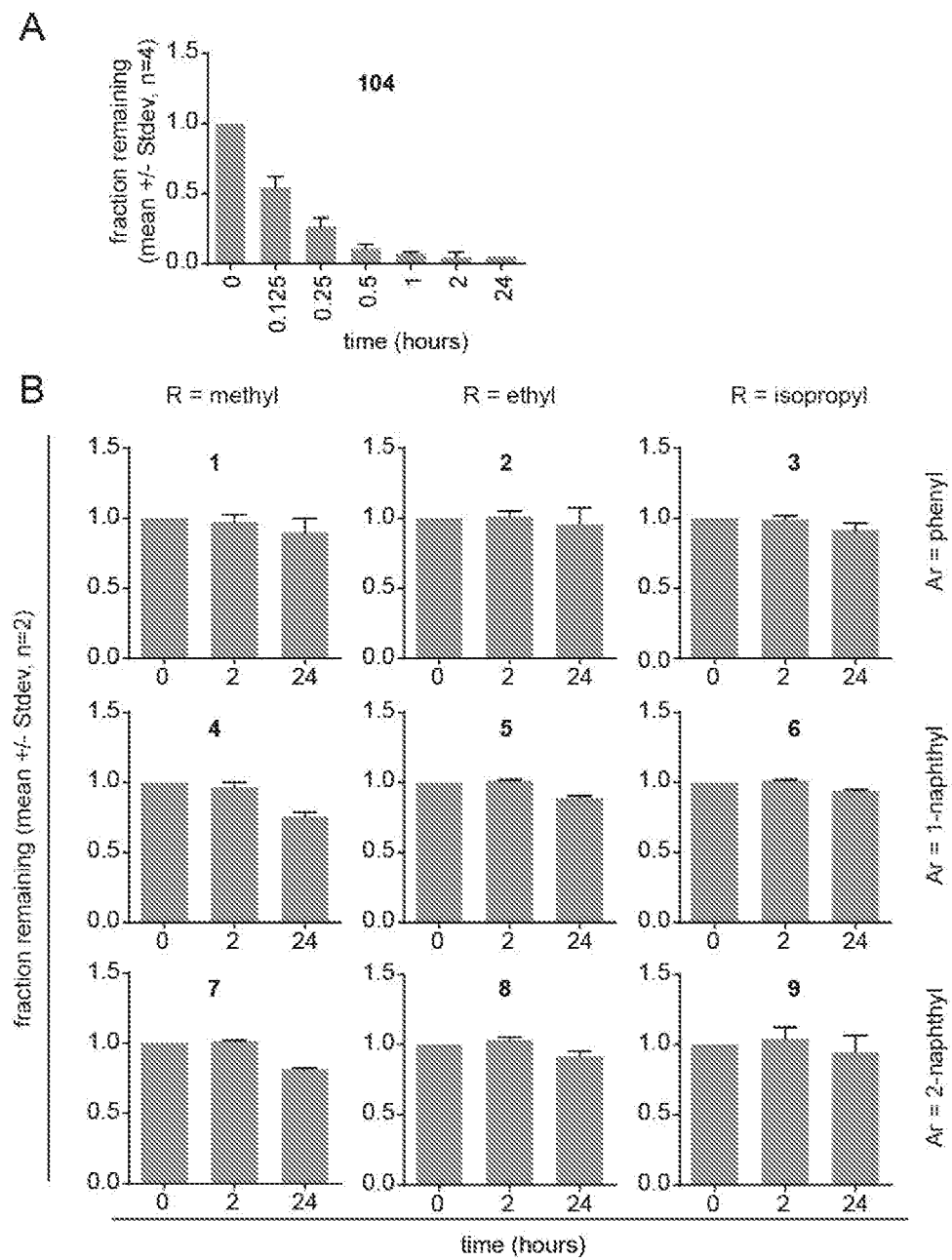
FIG. 1. Plasma stability of phosphonamidate prodrugs. A) $POM_2$-C-HMBP was exposed to 50% pooled human plasma in PBS for indicated time points. The graph indicates the mean fraction remaining and error bars represent standard deviations. Each data point was evaluated 2-4 independent times. B) The stability of the indicated phosphonamidates at 2 or 24 hour time points. Each data point was evaluated 2 independent times.
Figure 2A:
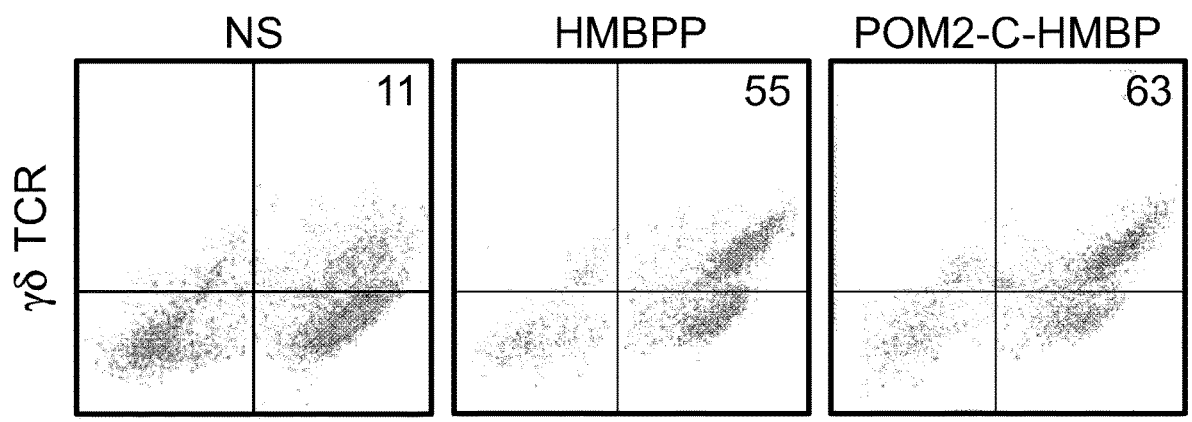
FIG. 2. Expansion of Vγ9Vδ2 T cells from PBMCs by phosphonamidate prodrugs. A) Following 3 days of compound exposure and 11 days of proliferation, the number of Vγ9Vδ2 T cells was assessed. Data are representative of 3 independent experiments using a concentration of 100 nM of each positive control and each test compound. B) Compounds were assessed for activity in dose response experiments, in comparison to non-stimulated cells (NS) and the positive controls HMBPP (HM) and $POM_2$-C-HMBP (POM2) at 100 nM. Data shown is from three independent experiments each using a minimum of two different human donors.
Figure 2A:
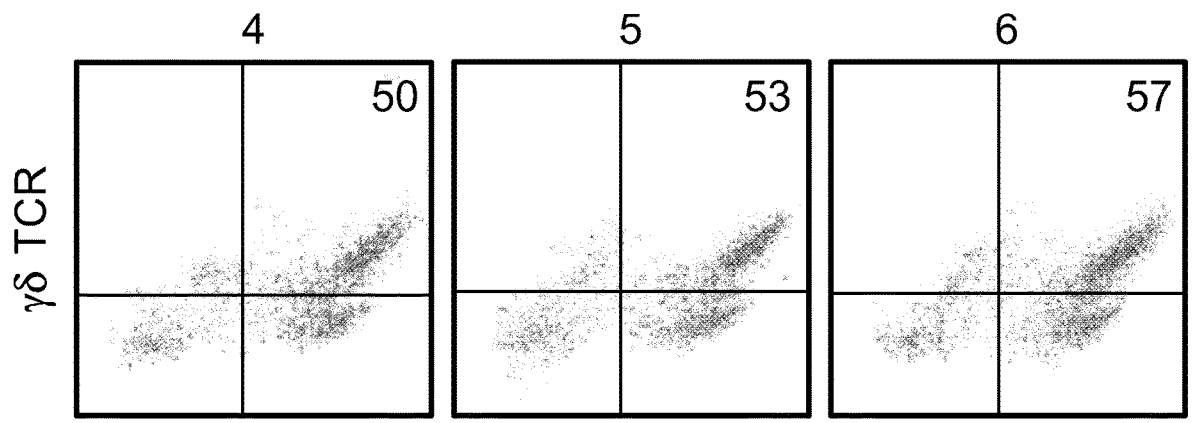
Figure 2A:
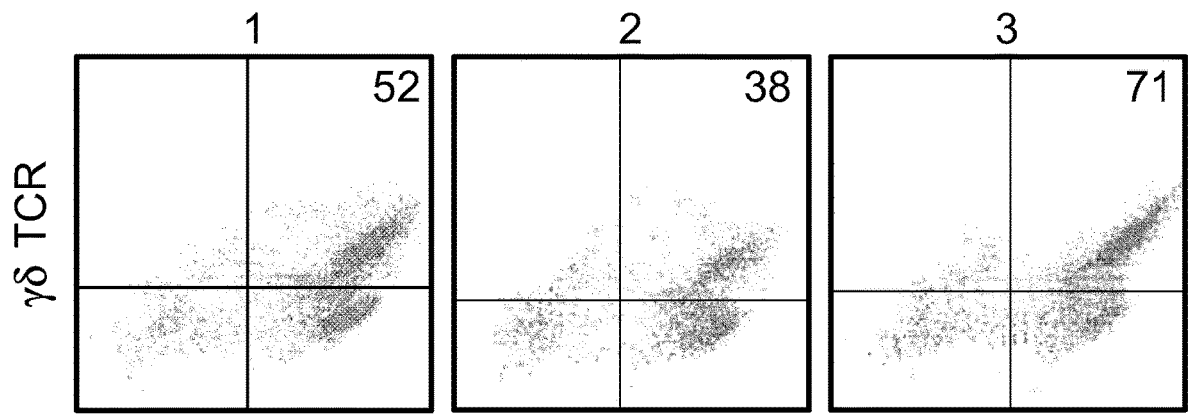
Figure 2A:
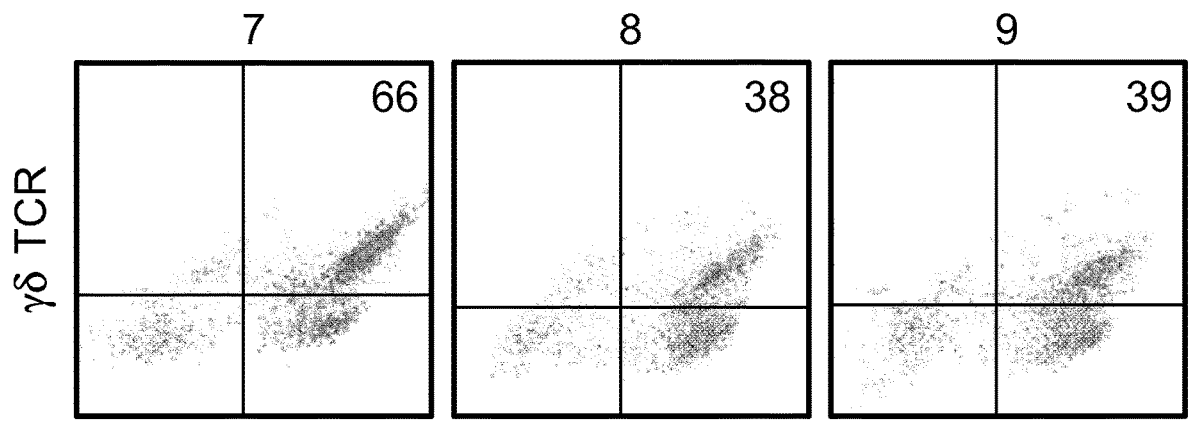
Figure 2B:
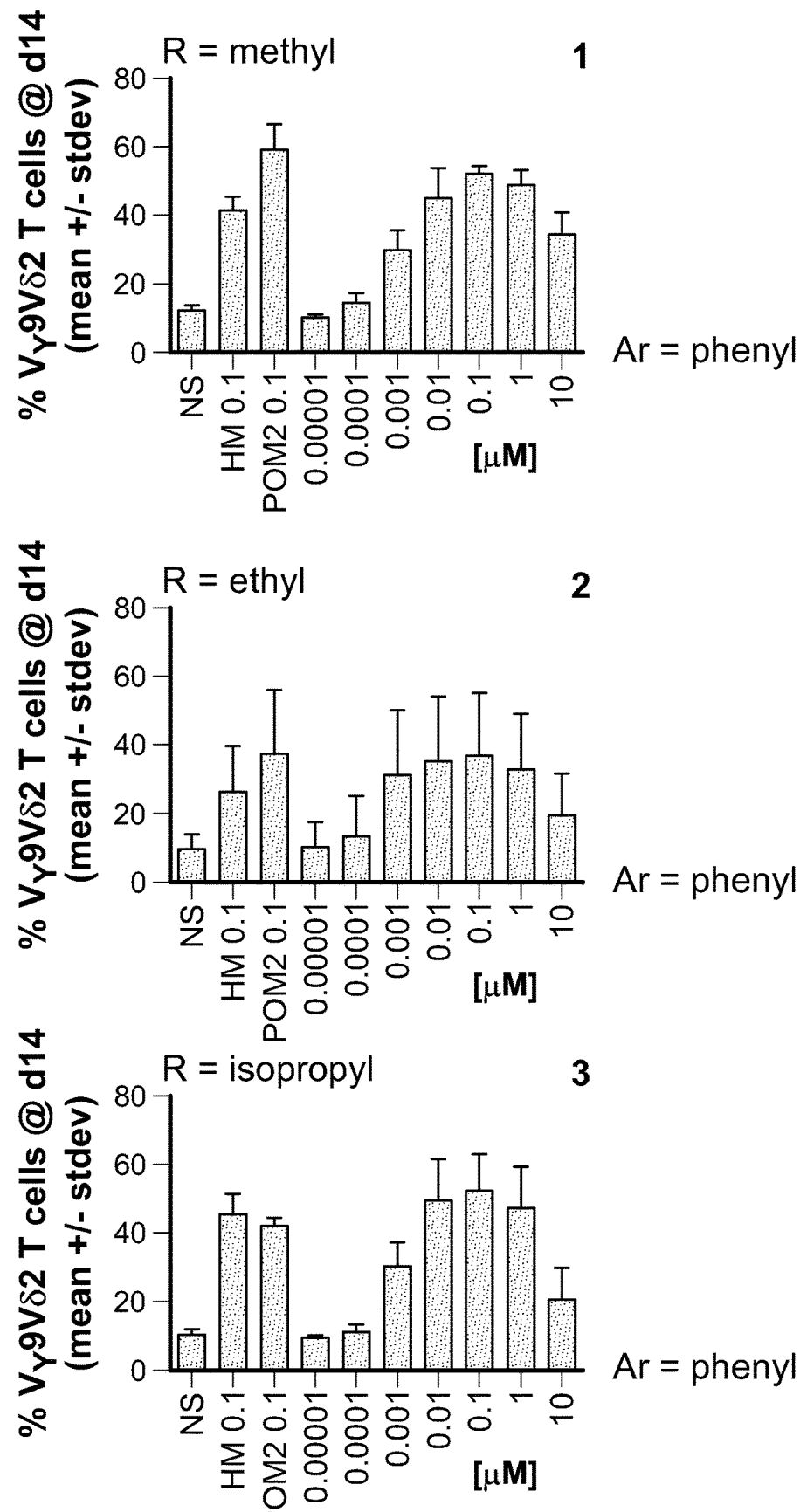
Figure 2B:
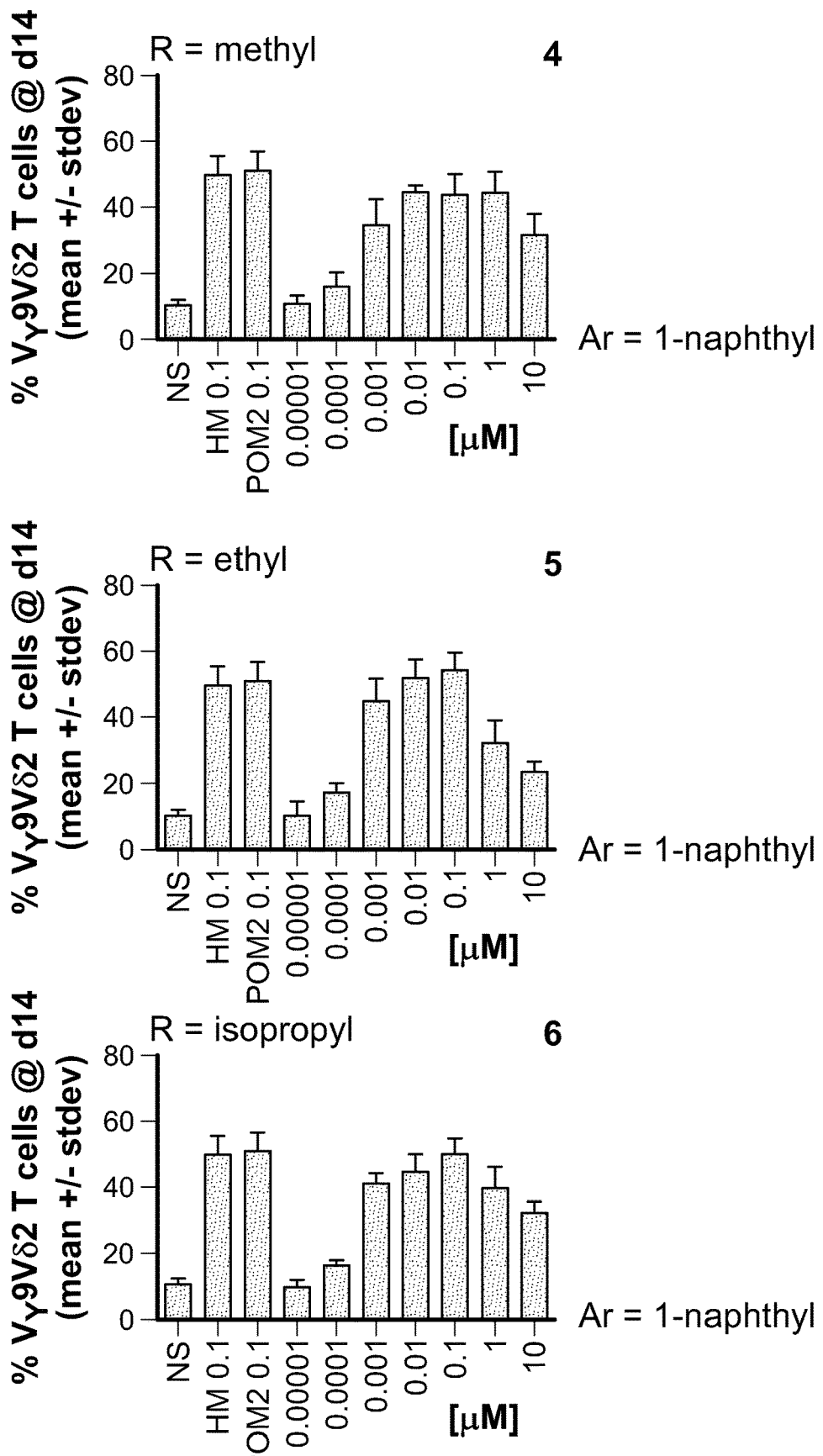
Figure 2B:
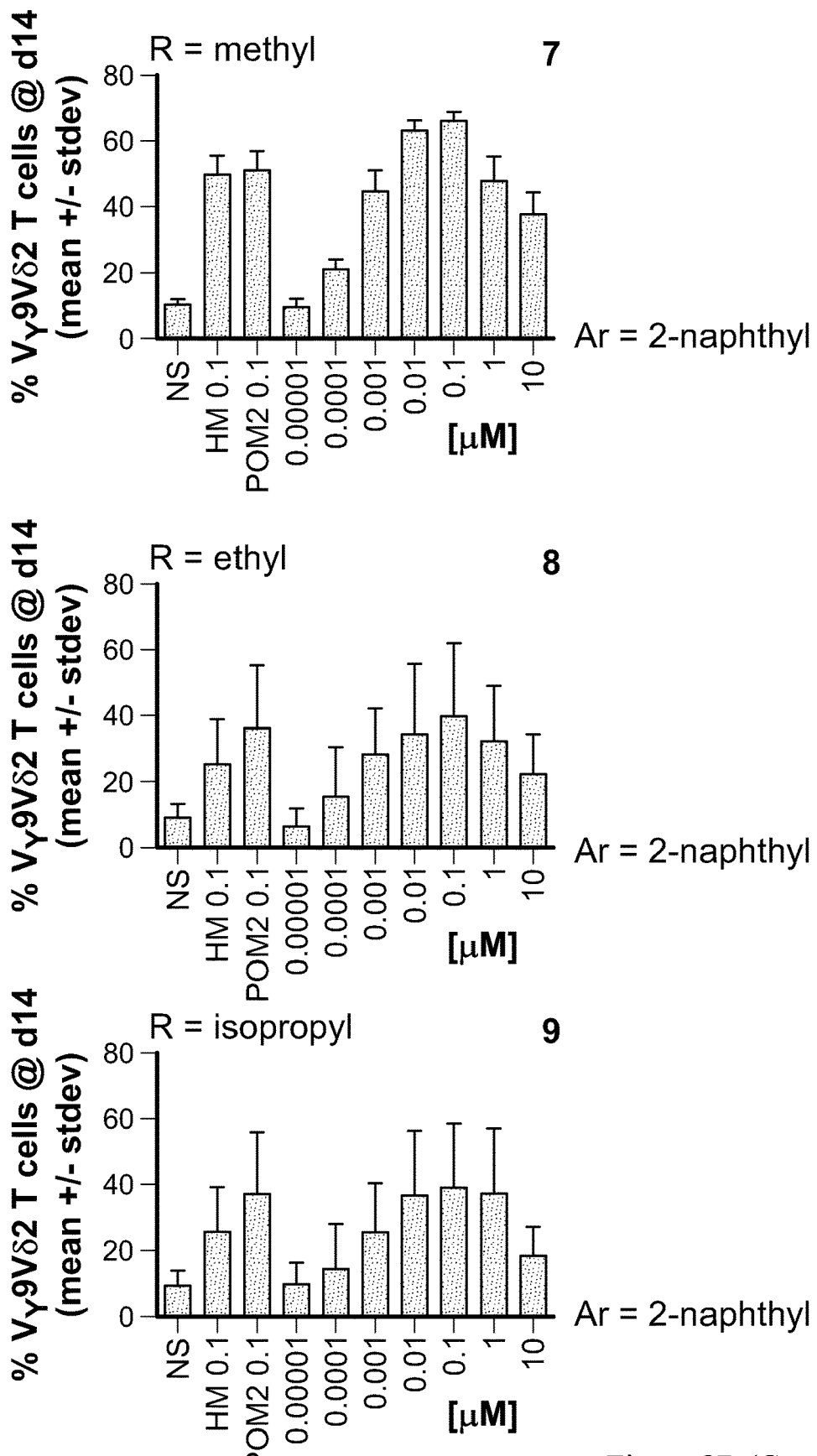

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$—C)carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "5-6 membered heteroaryl" as used herein refers to a single 5- or 6-membered aromatic ring that has at least one atom other than carbon in the ring, wherein the atom is selected from the group consisting of oxygen, nitrogen and sulfur; The sulfur and nitrogen atoms may also be present in an oxidized form provided the ring is aromatic. Exemplary heteroaryl ring systems include but are not limited to pyridyl, pyrimidinyl, oxazolyl and furyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

The term aryl($C_1-C_6$)alkyl, refers to a ($C_1-C_6$)alkyl group that is substituted with one or more (e.g. 1, 2, or 3) aryl groups.

The term (5-6 membered heteroaryl)($C_1-C_6$)alkyl, refers to a ($C_1-C_6$)alkyl group that is substituted with one or more (e.g. 1, 2, or 3) 5-6 membered heteroaryl groups.

The term "side chain of a natural amino acid" includes those side-chain groups found in (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; and (ii) all enantiomers, diastereomers, isomerically enriched, isotopically labelled (e.g. 2H, 3H, 14C, 15N), protected forms, and racemic mixtures thereof. For example, the term includes: hydrogen, methyl, —$CH_2SH$, —$CH_2SSCH_2$ ($NH_2$)COOH, —$CH_2CH_2$COOH, imidazole-5-ylmethyl, —$CH_2CH_2$CH(OH)$CH_2NH_2$, —$CH_2CONH_2$, —$CH_2$COOH, —$CH_2CH_2CONH_2$, —$(CH_2)_3$NHC(=NH)$NH_2$, 4-hydroxyprolin-2-yl, —CH($CH_3$)$CH_2CH_3$, —$CH_2$CH($CH_3$)$_2$, —$(CH_2)_4NH_2$, —$(CH_2)_2SCH_3$, benzyl, 2-prolinyl, —$CH_2$OH, —CH(OH) $CH_3$, 3-indolylmethyl, 4-hydroxybenzyl, and —CH($CH_3$)$_2$ As used herein a wavy line "~~" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; and aryl can be phenyl, indenyl, or naphthyl.

In one embodiment, the invention provides a compound of formula I or a salt thereof, wherein:
$R^1$ is aryl or aryl$(C_1-C_6)$alkyl, wherein any aryl and aryl$(C_1-C_6)$alkyl is optionally substituted with one or more groups $R^x$ independently selected from the group consisting of hydroxyl, halo, nitro, cyano, carboxy, $NR^aR^b$, $(C_1-C_6)$alkyl, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy, wherein any $(C_1-C_6)$alkyl and $(C_1-C_6)$alkoxy of $R^x$ is optionally substituted with one or more groups independently selected from halo;
$R^2$ is $(C_1-C_6)$alkyl that is optionally substituted with one or more groups independently selected from the group consisting of hydroxy, halo, nitro, cyano, carboxy, $NR^cR^d$, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy;
$R^3$ is oxo (=O) or hydroxy;
$R^4$ is the side-chain of a natural amino acid;
each $R^a$ and $R^b$ is independently selected from the group consisting of H, $(C_1-C_6)$alkyl, $(C_3-C_6)$cycloalkyl, and $(C_3-C_6)$cycloalkyl$(C_1-C_6)$alkyl; or Rand $R^b$ together with the nitrogen to which they are attached form a aziridino, azetidino, morpholino, piperazino, pyrrolidino or piperidino; and
each $R^c$ and $R^d$ is independently selected from the group consisting of H, $(C_1-C_6)$alkyl, $(C_3-C_6)$cycloalkyl, and $(C_3-C_6)$cycloalkyl$(C_1-C_6)$alkyl; or $R^c$ and $R^d$ together with the nitrogen to which they are attached form a aziridino, azetidino, morpholino, piperazino, pyrrolidino or piperidino.

In one embodiment $R^1$ is phenyl that is optionally substituted with one or more groups $R^x$ independently selected from the group consisting of hydroxy, halo, nitro, cyano, carboxy, $NR^aR^b$, $(C_1-C_6)$alkyl, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy, wherein any $(C_1-C_6)$alkyl and $(C_1-C_6)$alkoxy of $R^x$ is optionally substituted with one or more groups independently selected from halo.

In one embodiment $R^1$ is phenyl.

In one embodiment $R^1$ is naphthyl that is optionally substituted with one or more groups $R^x$ independently selected from the group consisting of hydroxy, halo, nitro, cyano, carboxy, $NR^aR^b$, $(C_1-C_6)$alkyl, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy, wherein any $(C_1-C_6)$alkyl and $(C_1-C_6)$alkoxy of $R^x$ is optionally substituted with one or more groups independently selected from halo.

In one embodiment $R^1$ is naphthyl.

In one embodiment $R^2$ is $(C_1-C_6)$alkyl.

In one embodiment $R^2$ is methyl, ethyl, or isopropyl.

Processes for preparing compounds of formula I are provided as further embodiments of the invention and are illustrated by the following procedures in which the meanings of the generic radicals are as given above unless otherwise qualified.

A compound of formula I or a pharmaceutically acceptable salt thereof, can be prepared using known intermediates and processes.

In cases where compounds are sufficiently basic or acidic, a salt of a compound of formula I can be useful as an intermediate for isolating or purifying a compound of formula I.

Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound to of the invention to bind to or to activate T-cells can be evaluated as described by Faust, B., et al., *ACS Med. Chem. Lett.,* 2017; Wiemer D. F.; Wiemer, A. J. *Biochemical Pharmacology,* 2014, 89, 301-312; Hsiao C, et al., *Chemistry and Biology,* 2014, 21, 945-954; and Nguyen, K., et al., *FASEB J.* 2017, 31, 4697-4706.

The invention will now be illustrated by the following non-limiting Examples.

General Experimental Procedures. Acetonitrile was distilled from calcium hydride prior to use and dimethylformamide (DMF), pyridine, and triethylamine ($Et_3N$) were dried over 4 Å molecular sieves (5% w/v). All other reagents and solvents were purchased from commercial sources and used without further purification. All reactions in non-aqueous solvents were conducted in flame-dried glassware under a positive pressure of argon and with magnetic stirring. For TLC analyses, pre-coated silica polyester backed plates (200 μm thickness, UV254 indicator) were visualized under both short-wave ultraviolet light (254 nm) and by heating post exposure top-anisaldehyde stain (93 parts 200 proof ethanol: 3.5 parts sulfuric acid: 1 part acetic acid: 2.5 parts p-anisaldehyde). Flash column chromatography was carried out using silica gel (60 Å, 40-63 m). Glass columns were slurry-packed using the appropriate eluent with the sample either being loaded as a concentrated solution in the same eluent or pre-adsorbed onto silica gel. Fractions containing the product were identified by TLC, combined and the solvent was removed under reduced pressure. The purity of the final compounds was corroborated by HPLC analysis using an Agilent 1120 infinity LC solvent delivery system with a variable wavelength UV detector. Compounds to be used for bioassay were eluted from a C18 column (either 5 μm, 250×10 mm or 8 μm, 250×10.0 mm) as analytical columns at a flow rate of 2.0 mL/min using 100% HPLC grade methanol (isocratic, 12 minutes). Compounds for bioassay were >95% pure at 254 nm. All NMR spectra were obtained at either 400 or 500 MHz for $^1H$, 100 or 125 MHz for $^{13}C$, and 161 or 202 MHz for $^{31}P$ with internal standards of $(CH_3)_4Si$ ($^1H$, 0.00 ppm) or $CDCl_3$ ($^1H$, 7.27; $^{13}C$, 77.2 ppm) or $CD_3OD$ ($^1H$, 3.31; $^{13}C$, 49.0 ppm) or $CD_3C(O)CD_3$ ($^1H$, 2.05; $^{13}C$, 206.3 ppm) or $CD_3CN$ ($^1H$, 1.94; $^{13}C$, 118.3 ppm) for non-aqueous samples or $D_2O$ ($^1H$, 4.80 ppm) for aqueous samples.[41] The $^{31}P$ chemical shifts are reported in ppm relative to 85% $H_3PO_4$ (external standard). High-resolution mass spectra were obtained by TOF MS ES+ at the University of Iowa Mass Spectrometry Facility.

EXAMPLES

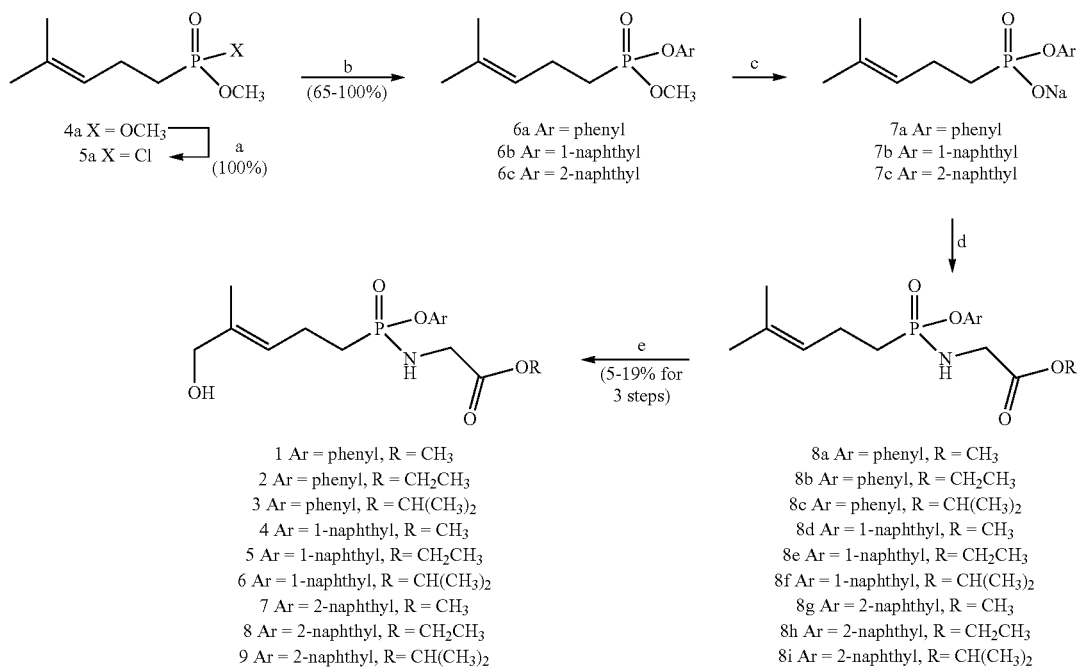

General Scheme for the Preparation of Examples 1-9

Reagents and conditions: (a) $(COCl)_2$, DMF (5 mol %), $CH_2Cl_2$, 0° C. to room temperature, overnight; (b) ArOH, $Et_3N$, THF or toluene, 0° C. to room temperature; (c) NaI, $H_3CCN$, reflux, overnight; (d) GlyOR·HCl, $PPh_3$, 2,2′-dithiodipyriding, pyridine, 60° C., overnight; (e) $SeO_2$, 70% aqueous tert-BuOOH, pyridine, methanol, 0° C. to room temperature, overnight.

Compounds of the invention can be prepared using starting materials, reagents, and techniques that are known, for example, see Foust, B. J., et al., *ACS Med. Chem. Lett.* 2017, 8, 914-918; Mackman, R. L., et al., *Bioorg. Med. Chem.* 2010, 18, 3606-3617; Camps, F., et al., *Synthesis-Stuttgart* 1978, 215-216; and Tang, X., et al., *Bioorg. Med. Chem. Lett.* 2018, 26, 1314-1319.

Example 1. Preparation of Methyl 2-[[[(E)-5-hydroxy-4-methyl-pent-3-enyl]-phenoxy-phosphoryl]amino]acetate (1)

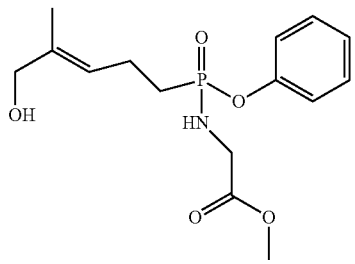 [SMILES: COC(=O)CNP(=O)(CC/C=C(\C)CO)Oc1ccccc1]

Using a procedure similar to that described in Example 2, the mixed ester 6a (1.1 g, 4.6 mmol) affords the intermediates 7a and 8a, and then compound 1 (25 mg, 5% over three steps) as a yellow oil: $^1$H NMR (500 MHz, CD$_3$OD) δ 7.37-7.33 (m, 2H), 7.22-7.15 (m, 3H), 5.49 (t, J=7.1 Hz, 1H), 3.93 (s, 2H), 3.81-3.70 (m, 2H), 3.68 (s, 3H), 2.50-2.43 (m, 2H), 2.06-1.98 (m, 2H), 1.69 (s, 3H); $^{13}$C NMR (125 MHz, CD$_3$OD) δ 173.4 (d, $J_{PC}$=4.3 Hz), 151.9 (d, $J_{PC}$=9.6 Hz), 137.3, 130.7 (2C), 125.9, 125.1 (d, $J_{PC}$=17.1 Hz), 121.9 (d, $J_{PC}$=3.9 Hz, 2C), 68.6, 52.5, 43.0, 28.9 (d, $J_{PC}$=129.8 Hz), 21.6 (d, $J_{PC}$=4.2 Hz), 13.7; $^{31}$P NMR (161 MHz, CD$_3$OD) δ+35.1; HRMS (ES+, m/z) calcd. for (M+H)$^+$ C$_{15}$H$_{23}$NO$_5$P: 328.1314; found: 328.1322.

The intermediate 6a was prepared as described in Foust, B. J., et al., *ACS Med. Chem. Lett.* 2017, 8, 914-918.

Example 2. Preparation of Ethyl 2-[[[(E)-5-hydroxy-4-methyl-pent-3-enyl]-phenoxy-phosphoryl]amino]acetate (2)

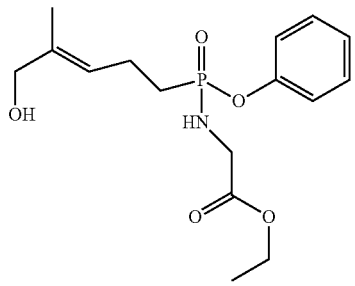 [SMILES: CCOC(=O)CNP(=O)(CC/C=C(\C)CO)Oc1ccccc1]

The mixed ester 6a (1.1 g, 4.3 mmol) was dissolved in freshly distilled acetonitrile (14 mL) and added as a solution to solid, flame-dried sodium iodide (645 mg, 4.3 mmol). The resultant solution was heated at reflux overnight, allowed to cool to room temperature, and then concentrated under reduced pressure to reveal a pale yellow to white solid (7a).

Glycine ethyl ester HCl (1.1 g, 7.7 mmol) was added followed by anhydrous pyridine (21 mL) and then triethylamine (6.4 mL, 45.6 mmol) and the resulting solution was stirred. In a separate flask 2,2'-dithiodipyridine (6.9 g) and PPh$_3$ (5.9 g) were dissolved in anhydrous pyridine (21 mL) and the resultant solution was stirred for 20 minutes. This solution was added to the solution of monosodium salt and the mixture was stirred overnight at 60° C. The reaction mixture was concentrated under reduced pressure and the residue was dissolved in EtOAc and filtered. The filtrate was concentrated under reduced pressure and the residue subjected to silica gel chromatography (0-10% EtOAc in Et$_2$O) to provide the desired monoamidate 8b as a clear to pale yellow oil.

In a separate flask, SeO$_2$ (89 mg, 0.8 mmol) and pyridine (0.5 mL, 6.0 mmol) were dissolved in 70% aqueous tert-butyl hydroperoxide solution (0.9 mL), stirred for 30 minutes at room temperature and cooled to 0° C. The aforementioned monoamidate oil was dissolved in MeOH (2.5 mL), added to the solution of oxidant and the reaction mixture was stirred for 18 hours. The solution was concentrated under reduced pressure and the residue was dissolved in EtOAc, washed with aqueous potassium carbonate (2×) and then brine, dried with MgSO$_4$, and filtered. The filtrate was concentrated under reduced pressure and the residue subjected to silica gel chromatography (0-20% acetone in CH$_2$Cl$_2$) to provide Example 2 (30 mg, 8% over three steps) as a yellow oil: $^1$H NMR (500 MHz, CD$_3$OD) δ 7.36-7.33 (m, 2H), 7.22-7.16 (m, 3H), 5.49 (t, J=7.1 Hz, 1H), 4.14 (q, J=7.1 Hz, 2H), 3.93 (s, 2H), 3.79-3.62 (m, 2H), 2.51-2.43 (m, 2H), 2.06-1.99 (m, 2H), 1.69 (s, 3H), 1.24 (t, J=7.1 Hz, 3H); $^{13}$C NMR (125 MHz, CD$_3$OD) δ 172.9, 151.9 (d, $J_{CP}$=9.4 Hz), 137.3, 130.7 (2C), 125.9, 125.1 (d, $J_{CP}$=17.6 Hz), 121.9 (d, $J_{CP}$=4.5 Hz, 2C), 68.6, 62.2, 43.2, 28.9 (d, $J_{CP}$=129.1 Hz), 21.6 (d, $J_{CP}$=4.0 Hz), 14.5, 13.7; $^{31}$P NMR (202 MHz, CD$_3$OD) δ+35.0; HRMS (ES+, m/z) calcd. for (M+H)$^+$ C$_{16}$H$_{25}$NO$_5$P: 342.1470; found: 342.1462.

Example 3. Preparation of Isopropyl 2-[[[(E)-5-hydroxy-4-methyl-pent-3-enyl]-phenoxy-phosphoryl]amino]acetate (3)

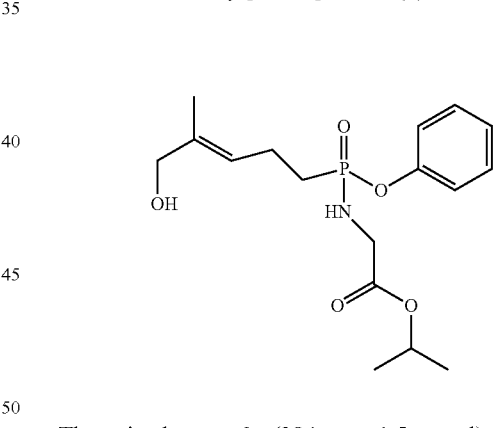

The mixed ester 6a (384 mg, 1.5 mmol) was treated according to the general procedure for prodrug preparation to afford phosphonamidate 9c (99 mg, 19% over three steps) as a yellow oil, along with 88 mg of the corresponding aldehyde: $^1$H NMR (400 MHz, CD$_3$C(O)CD$_3$) δ 7.34 (t, J=7.3 Hz, 2H), 7.26 (d, J=7.7 Hz, 2H), 7.15 (t, J=7.5 Hz, 1H), 5.49 (td, J=7.2, 1.1 Hz, 1H), 4.97 (sept, J=6.2 Hz, 1H), 4.57-4.51 (m, 1H), 3.92 (s, 2H), 3.83-3.62 (m, 2H), 2.49-2.39 (m, 2H), 2.01-1.93 (m, 2H), 1.65 (s, 3H), 1.20 (d, J=6.2, Hz, 3H), 1.20 (d, J=6.3, Hz, 3H); $^{13}$C NMR (125 MHz, CD$_3$CN) δ 171.7 (d, $J_{CP}$=5.0 Hz), 151.8 (d, $J_{CP}$=8.9 Hz), 137.3 (d, $J_{CP}$=1.4 Hz), 130.6 (2C), 125.4, 124.2 (d, $J_{CP}$=16.1 Hz), 121.8 (d, $J_{CP}$=4.0 Hz, 2C), 69.5, 68.0, 43.4, 28.6 (d, $J_{CP}$=128.7 Hz), 22.0 (2C), 21.3 (d, $J_{CP}$=4.4 Hz), 13.8; $^{31}$P (202 MHz, CD$_3$CN) δ+32.9; HRMS (ES+, m/z) calcd. for (M+Na)$^+$ C$_{17}$H$_{26}$NNaO$_5$P: 378.1446; found: 378.1448.

Example 4. Preparation of Methyl 2-[[[(E)-5-hydroxy-4-methyl-pent-3-enyl]-(1-naphthyloxy)phosphoryl]amino]acetate (4)

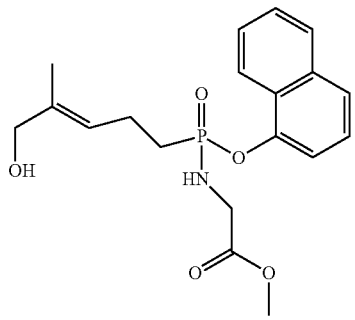 [SMILES: COC(=O)CNP(=O)(CC/C=C(\C)CO)Oc1cccc2ccccc12]

The mixed ester 6b (1.012 g, 3.3 mmol) was treated according to the general procedure to obtain phosphonate 9d (86 mg, 14% over three steps) as an amber oil: $^1$H NMR (400 MHz, CD$_3$OD) δ 8.17-8.15 (m, 1H), 7.89-7.86 (m, 1H), 7.69 (d, J=8.1 Hz, 1H), 7.57-7.51 (m, 2H), 7.50 (d, J=7.7 Hz, 1H), 7.42 (t, J=7.9 Hz, 1H), 5.51 (t, J=6.4 Hz, 1H), 3.92 (s, 2H), 3.80-3.66 (m, 2H), 3.61 (s, 3H), 2.56-2.50 (m, 2H), 2.20-2.12 (m, 2H), 1.65 (s, 3H); $^{13}$C NMR (100 MHz, CD$_3$OD) δ 173.3 (d, $J_{CP}$=4.0 Hz), 147.8 (d, $J_{CP}$=9.6 Hz), 137.4, 136.3, 128.9, 128.2, 127.7, 127.4, 126.6, 125.7, 125.0 (d, $J_{CP}$=17.6 Hz), 122.8, 116.7 (d, $J_{CP}$=3.8 Hz), 68.6, 52.5, 43.0, 28.9 (d, $J_{CP}$=131.3 Hz), 21.7 (d, $J_{CP}$=4.1 Hz), 13.6; $^{31}$P NMR (161 MHz, CD$_3$OD) δ+35.6; HRMS (ES+, m/z) calcd. for (M+Na)$^+$ C$_{19}$H$_{24}$NNaO$_5$P: 400.1290; found: 400.1289.

The intermediate 6b was prepared as described in Foust, B. J., et al., ACS Med. Chem. Lett. 2017, 8, 914-918

Example 5. Preparation of Ethyl 2-[[[(E)-5-hydroxy-4-methyl-pent-3-enyl]-(1-naphthyloxy)phosphoryl]amino]acetate (5)

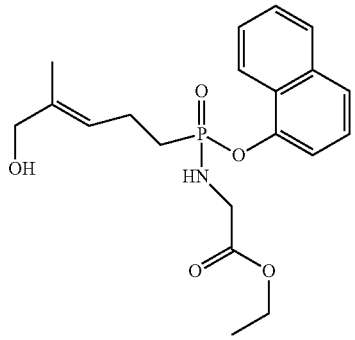 [SMILES: CCOC(=O)CNP(=O)(CC/C=C(\C)CO)Oc1cccc2ccccc12]

The mixed ester 6b (932 mg, 3.1 mmol) was treated according to the general procedure to afford phosphonamidates 9e (40 mg, 9% over three steps) as an amber oil: $^1$H NMR (400 MHz, CD$_3$OD) δ 8.17-8.15 (m, 1H), 7.89-7.87 (m, 1H), 7.69 (d, J=8.1 Hz, 1H), 7.57-7.50 (m, 2H), 7.49 (d, J=7.6 Hz, 1H), 7.42 (d, J=7.9 Hz, 1H), 5.51 (td, J=7.1, 1.1 Hz, 1H), 4.08 (q, J=7.1 Hz, 2H), 3.92 (s, 2H), 3.82-3.61 (m, 2H), 2.59-2.46 (m, 2H), 2.20-2.12 (m, 2H), 1.65 (s, 3H), 1.18 (t, J=7.1 Hz, 3H); $^{13}$C NMR (100 MHz, CD$_3$OD) δ 172.8 (d, $J_{CP}$=4.0 Hz), 147.8 (d, $J_{CP}$=9.5 Hz), 137.4, 136.3, 128.9, 128.2 (d, $J_{CP}$=4.8 Hz), 127.7, 127.4, 126.6, 125.7, 125.0 (d, $J_{CP}$=17.9 Hz), 122.8, 116.7 (d, $J_{CP}$=3.8 Hz), 68.6, 62.1, 43.2, 28.9 (d, $J_{CP}$=127.7 Hz), 21.7 (d, $J_{CP}$=4.4 Hz), 14.4, 13.6; $^{31}$P NMR (161 MHz, CD$_3$OD) δ+35.6; HRMS (ES+, m/z) calcd. for (M+Na)$^+$ C$_{20}$H$_{26}$NNaO$_5$P: 414.1446; found: 414.1445.

Example 6. Preparation of Isopropyl 2-[[[(E)-5-hydroxy-4-methyl-pent-3-enyl]-(1-naphthyloxy)phosphoryl]amino]acetate (6)

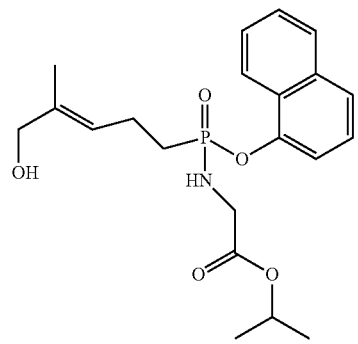 [SMILES: C/C(=C\CCP(=O)(NCC(=O)OC(C)C)Oc1cccc2ccccc12)CO]

The mixed ester 6b (915 mg, 3.0 mmol) was treated according to the general procedure to give phosphonamidates 9f (103 mg, 18% over three steps) as an amber oil: $^1$H NMR (400 MHz, CD$_3$OD) δ 8.17-8.15 (m, 1H), 7.88-7.86 (m, 1H), 7.68 (d, J=8.1 Hz, 1H), 7.57-7.50 (m, 2H), 7.49 (d, J=7.7 Hz, 1H), 7.41 (t, J=8.0 Hz, 1H), 5.51 (td, J=7.2, 1.2 Hz, 1H), 5.00-4.91 (sept, J=6.2 Hz, 1H), 3.92 (s, 2H), 3.79-3.58 (m, 2H), 2.57-2.48 (m, 2H), 2.20-2.12 (m, 2H), 1.65 (s, 3H), 1.18 (d, J=4.5 Hz, 3H), 1.17 (d, J=4.5 Hz, 3H); $^{13}$C NMR (100 MHz, CD$_3$OD) δ 172.3 (d, $J_{CP}$=4.3 Hz), 147.8 (d, $J_{CP}$=9.6 Hz), 137.4, 136.3, 128.9, 128.2 (d, $J_{CP}$=5.4 Hz), 127.7, 127.4, 126.6, 125.6, 125.0 (d, $J_{CP}$=17.4 Hz), 122.7, 116.6 (d, $J_{CP}$=3.8 Hz), 70.0, 68.5, 43.4, 28.9 (d, $J_{CP}$=128.4 Hz), 22.0, 21.9, 21.7 (d, $J_{CP}$=4.4 Hz), 13.7; $^{31}$P NMR (161 MHz, CD$_3$OD) δ+35.6; HRMS (ES+, m/z) calcd. for (M+Na)$^+$ C$_{21}$H$_{28}$NNaO$_5$P: 428.1603; found: 428.1599.

Example 7. Preparation of Methyl 2-[[[(E)-5-hydroxy-4-methyl-pent-3-enyl]-(2-naphthyloxy)phosphoryl]amino]acetate (7)

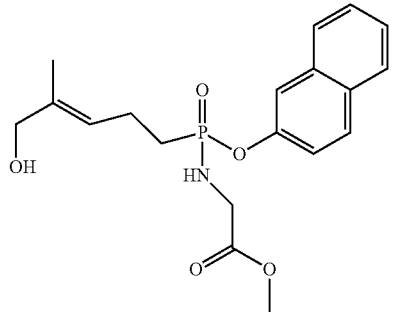 [SMILES: COC(=O)CNP(=O)(CC/C=C(\C)CO)Oc1ccc2ccccc2c1]

The mixed ester 6c (961 mg, 3.2 mmol) was treated according to the general procedure to afford the phosphonamidate 9g (59 mg, 11% over three steps) as an amber oil:

¹H NMR (400 MHz, CD$_3$OD) δ 7.86-7.83 (m, 2H), 7.80 (d, J=8.1 Hz, 1H), 7.69 (s, 1H), 7.48 (td, J=6.9, 1.2 Hz, 1H), 7.43 (td, J=6.9, 1.1 Hz, 1H), 7.37-7.35 (m, 1H), 5.51 (td, J=7.3, 1.0 Hz, 1H), 3.94 (s, 2H), 3.83-3.65 (m, 2H), 3.61 (s, 3H), 2.55-2.43 (m, 2H), 2.12-2.03 (m, 2H), 1.69 (s, 3H); ¹³C NMR (100 MHz, CD$_3$OD) δ 173.3 (d, $J_{PC}$=3.9 Hz), 149.5 (d, $J_{PC}$=9.6 Hz), 137.3, 135.4, 132.3, 130.8, 128.7, 128.4, 127.8, 126.5, 125.1 (d, $J_{PC}$=17.4 Hz), 122.0 (d, $J_{PC}$=4.4 Hz), 118.3 (d, $J_{PC}$=4.9 Hz), 68.6, 52.5, 43.0, 28.9 (d, $J_{PC}$=129.7 Hz), 21.6 (d, $J_{PC}$=4.2 Hz), 13.7; ³¹P NMR (161 MHz, CD$_3$OD) δ+35.4; HRMS (ES+, m/z) calcd. for (M+Na)$^+$ C$_{19}$H$_{24}$NNaO$_5$P: 400.1290; found: 400.1288.

The intermediate 6c was prepared as follows.

a. Methyl naphthalene-2-yl (4-methylpent-3-en-1-yl)phosphonate (6c)

A solution of 2-naphthol (1.91 g, 13.3 mmol) and triethylamine (1.84 mL, 13.3 mmol) in toluene (10 mL) was added dropwise to a solution of the acid chloride 5¹² (5.3 mmol) in toluene (10 mL) and allowed to react for 15 hours. The reaction then was diluted with diethyl ether (30 mL) and quenched by addition of brine (5 mL). The organic portion was then washed four times with 1 M NaOH (5 mL), dried (MgSO$_4$), filtered through celite, and concentrated in vacuo. The resulting reddish yellow oil was purified via chromatography (silica, 100% hexanes—40% EtOAc in hexanes) and the product 6c was concentrated to a yellow oil in 82% yield (1.32 g): ¹H NMR (400 MHz, CDCl$_3$) δ 7.79-7.78 (m, 3H), 7.68 (s, 1H), 7.46-7.41 (m, 2H), 7.35 (d, J=8.8 Hz, 1H), 5.13 (t, J=6.8 Hz, 1H), 3.81 (d, $J_{PH}$=11.2 Hz, 3H), 2.47-2.35 (m, 2H), 2.00-1.94 (m, 2H), 1.67 (s, 3H), 1.61 (s, 3H); ¹³C NMR (100 MHz, CDCl$_3$) δ 148.3 (d, $J_{PC}$=9.3 Hz), 134.0, 133.3, 130.9, 129.9, 127.7, 127.5, 126.7 125.4, 122.7 (d, $J_{PC}$=17.7 Hz), 120.5 (d, $J_{PC}$=4.4 Hz), 116.8 (d, $J_{PC}$=4.2 Hz), 52.8 (d, $J_{PC}$=6.1 Hz), 25.6, 25.6 (d, $J_{PC}$=136.9 Hz), 21.1 (d, $J_{PC}$=4.7 Hz), 17.7; ³¹P (161 MHz, CDCl$_3$) δ+30.5; HRMS (ES+, m/z) calcd. for (M+H)+ C$_{17}$H$_{22}$O$_3$P: 305.1307; found: 305.1304.

Example 8. Preparation of Ethyl 2-[[[(E)-5-hydroxy-4-methyl-pent-3-enyl]-(2-naphthyloxy)phosphoryl]amino]acetate (8)

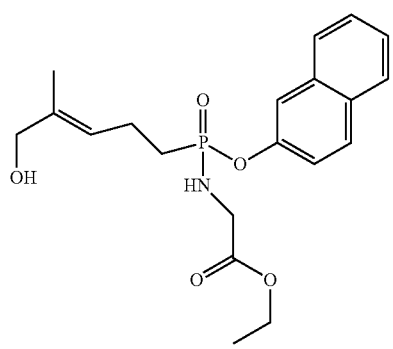 [SMILES: CCOC(=O)CNP(=O)(CC/C=C(\C)CO)Oc1ccc2ccccc2c1]

The mixed ester 6c (990 mg, 3.3 mmol) was treated according to the general procedure to afford compound 9h (58 mg, 9% over three steps) as an amber oil: ¹H NMR (500 MHz, CD$_3$OD) δ 7.88-7.85 (m, 2H), 7.81 (d, J=8.3 Hz, 1H), 7.69 (s, 1H), 7.51-7.48 (m, 1H), 7.46-7.43 (m, 1H), 7.37-7.35 (m, 1H), 5.51 (t, J=6.6 Hz, 1H), 4.09 (q, J=7.1 Hz, 2H), 3.94 (s, 2H), 3.81-3.63 (m, 2H), 2.55-2.44 (m, 2H), 2.12-2.05 (m, 2H), 1.70 (s, 3H), 1.18 (t, J=8.0 Hz, 3H); ¹³C NMR (125 MHz, CD$_3$OD) δ 172.8, 149.4 (d, $J_{CP}$=10.1 Hz), 137.3, 135.4, 132.3, 130.8, 128.7, 128.4, 127.8, 126.5, 125.0 (d, $J_{CP}$=17.2 Hz), 122.1 (d, $J_{CP}$=4.1 Hz), 118.2 (d, $J_{CP}$=4.3 Hz), 68.6, 62.1, 43.2, 28.9 (d, $J_{CP}$=128.6 Hz), 21.6 (d, $J_{CP}$=4.1 Hz), 14.4, 13.7; ³¹P NMR (202 MHz, CD$_3$OD) δ+35.4; HRMS (ES+, m/z) calcd. for (M+Na)$^+$ C$_{20}$H$_{26}$NNaO$_5$P: 414.1446; found: 414.1447.

Example 9. Preparation of Isopropyl 2-[[[(E)-5-hydroxy-4-methyl-pent-3-enyl]-(2-naphthyloxy)phosphoryl]amino]acetate (9)

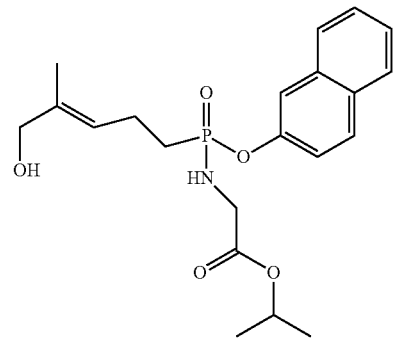 [SMILES: C/C(=C\CCP(=O)(NCC(=O)OC(C)C)Oc1ccc2ccccc2c1)CO]

The mixed ester 6c (999 mg, 3.3 mmol) was treated according to the general procedure to afford phosphonamidates 9i (137 mg, 10% over three steps) as an amber oil: ¹H NMR (500 MHz, CD$_3$OD) δ 7.85 (t, J=8.4 Hz, 2H), 7.80 (d, J=8.0 Hz, 1H), 7.69 (s, 1H), 7.48 (t, J=7.6 Hz, 1H), 7.44 (t, J=7.3 Hz, 1H), 7.36 (d, J=8.7 Hz, 1H), 5.51 (t, J=7.0 Hz, 1H), 4.95 (sept, J=6.2 Hz, 1H), 3.94 (s, 2H), 3.77-3.62 (m, 2H), 2.53-2.47 (m, 2H), 2.11-2.05 (m, 2H), 1.69 (s, 3H), 1.18 (d, J=7.0 Hz, 3H), 1.18 (d, J=6.9 Hz, 3H); ¹³C NMR (125 MHz, CD$_3$OD) δ 172.5 (d, $J_{CP}$=4.1 Hz), 149.6 (d, $J_{CP}$=10.1 Hz), 137.5, 135.5, 132.5, 130.9, 128.9, 128.6, 127.9, 126.6, 125.2 (d, $J_{CP}$=20.2 Hz), 122.1 (d, $J_{CP}$=4.1 Hz), 118.4 (d, $J_{CP}$=4.4 Hz), 70.2, 68.7, 43.6, 29.1 (d, $J_{CP}$=128.3 Hz), 22.1 (2C), 21.8 (d, $J_{CP}$=4.3 Hz), 13.9; ³¹P NMR (161 MHz, CD$_3$OD) δ+35.4; HRMS (ES+, m/z) calcd. for (M+H)$^+$ C$_{21}$H$_{29}$NO$_5$P: 406.1783; found: 406.1782.

Example 10. Identification of Aldehyde 10

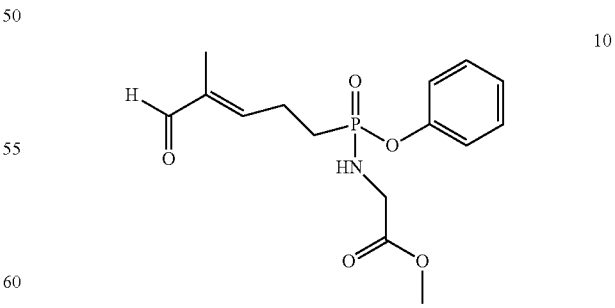

The aldehyde 10 was isolated as a by-product of the SeO$_2$ oxidation that gave compound 1. For the aldehyde 10: ¹H NMR (400 MHz, CD$_3$OD) δ 9.39 (s, 1H), 7.38-7.34 (m, 2H), 7.22-7.16 (m, 3H), 6.70 (tq, J=7.3, 1.3 Hz, 1H), 3.82-3.71 (m, 2H), 3.68 (s, 3H), 2.86-2.76 (m, 2H), 2.24-2.16 (m, 2H), 1.77 (s, 3H); $^{13}$C NMR (125 MHz, CD$_3$OD) δ 196.9, 173.4 (d, J$_{PC}$=4.0 Hz), 154.5 (d, J$_{PC}$=15.5 Hz), 151.7, 141.0, 130.8 (2C), 126.0, 121.9 (d, J$_{PC}$=4.6 Hz, 2C), 52.5, 43.0, 27.6 (d, J$_{PC}$=132.0 Hz), 23.1 (d, J$_{PC}$=4.2 Hz), 9.1; $^{31}$P NMR (161 MHz, CD$_3$OD) δ+33.9; HRMS (ES+, m/z) calcd. for (M+Na)$^+$ C$_{15}$H$_{20}$NNaO$_5$P: 348.0977; found: 348.0983.

Example 11. Identification of Aldehydes 11 and 12

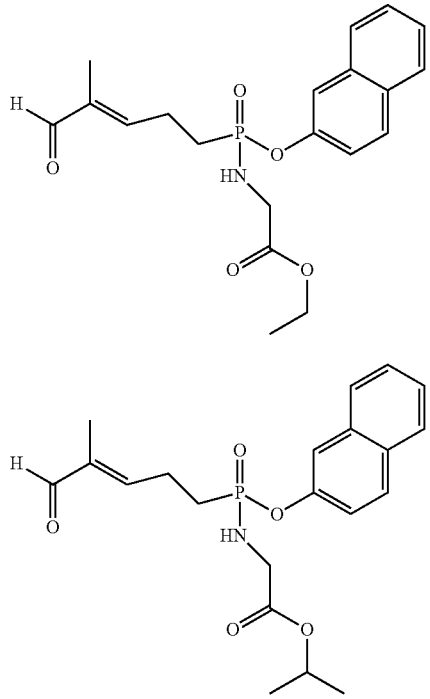

The aldehydes 11 and 12 were also isolated as a by-product of the SeO$_2$ oxidations that gave compounds 8 and 9.

Example 12 Biological Assays

Materials and supplies. Human peripheral blood mononuclear cell (PBMCs) were isolated from buffy coat obtained from Research Blood Components (Boston, MA). K562 cells were from the American Type Culture Collection or Sigma Aldrich. The FITC-conjugated anti-γδ-TCR (5A6.E91) antibody and pooled human plasma was purchased from Fisher (Waltham, MA). The phycoerythrin conjugated anti-CD3 (UCHT1) antibody and interferon γ enzyme-linked immunosorbent assay kit were purchased from Biolegend (San Diego, CA). The CellQuanti-Blue Cell Viability Assay Kit was purchased from BioAssay Systems (Hayward, CA). HMBPP was purchased from Echelon (Salt Lake City, UT). The TCRγ/δ+ T Cell Isolation Kit was from Miltenyi (Bergisch Gladbach, Germany). POM$_2$-C-HMBP was synthesized as described previously.[9]

Expansion of Vγ9Vδ2 T cells. All compounds were evaluated for their ability to promote growth of human Vγ9Vδ2 T cells from peripheral blood as described previously (see Hsiao, C. H., et al., Chem. Biol. 2014, 21, 945-954; and Shippy, R. R., et al., J. Med. Chem. 2017, 60, 2373-2382.) In each experiment, 100 nM of HMBPP and 100 nM of POM$_2$-C-HMBP were used as positive controls. Negative controls contained cells with interleukin 2 in the absence of test compounds. EC$_{50}$ values were determined as the concentration that induced 50% of the maximum proliferative effect. All experiments were performed at least three times using cells from at least two different donors. Data for representative compounds of the invention is shown in Table 1 see FIG. 2).

TABLE 1

Activity of test compounds for expansion of Vγ9Vδ2 T cells from peripheral blood mononuclear cells following 72 hour compound exposure.

| Compound | cLogP[a] | EC$_{50}$ [μM] (95% CI) | Fold difference vs cmpd 10 | Fold difference vs cmpd 11 |
|---|---|---|---|---|
| 100 | −0.24 | 4.0 | NA[a] | NA |
| 101 | 0.31 | >10 | NA | NA |
| 102 | 3.56 | 0.014 | 290 | ND[a] |
| 103 | 4.72 | 0.00079 | 5100 | 6.8 |
| 104 | 3.42 | 0.0054 | 740 | NA |
| 1 | 1.67 | 0.0015 (0.00038 to 0.0057) | 2700 | 3.6 |
| 2 | 2.05 | 0.00036 (0.00022 to 0.00059) | 11000 | 15 |
| 3 | 2.41 | 0.0011 (0.00066 to 0.0017) | 3600 | 4.9 |
| 4 | 2.83 | 0.00044 (0.00026 to 0.00076) | 9100 | 12 |
| 5 | 3.21 | 0.00036 (0.00024 to 0.00053) | 11000 | 15 |
| 6 | 3.57 | 0.00034 (0.000095 to 0.0012) | 12000 | 16 |
| 7 | 2.86 | 0.00058 (0.00029 to 0.0012) | 6900 | 9.3 |
| 8 | 3.23 | 0.00053 (0.000052 to 0.0054) | 7500 | 10 |
| 9 | 3.60 | 0.00082 (0.00048 to 0.0014) | 4900 | 6.6 |
| Mean Ar = phenyl | NA | 0.00099 | NA | NA |
| Mean Ar = 1-naphthyl | NA | 0.00038 | NA | NA |
| Mean Ar = 2-naphthyl | NA | 0.00064 | NA | NA |
| Mean R = methyl | NA | 0.00084 | NA | NA |
| Mean R = ethyl | NA | 0.00042 | NA | NA |
| Mean R = isopropyl | NA | 0.00075 | NA | NA |

[a]cLogP values were determined from http://www.molinspiration.com/cgi-bin/properties, ND = not determined, NA = not applicable. Compounds 101, 102, and 104 were prepared as described by Hsiao, C. H., et al., Chem. Biol. 2014, 21, 945-954. Compounds 103 and 104 were prepared as described by Foust, B. J., et al., ACS Med. Chem. Lett. 2017, 8, 914-918.

Figure 4:
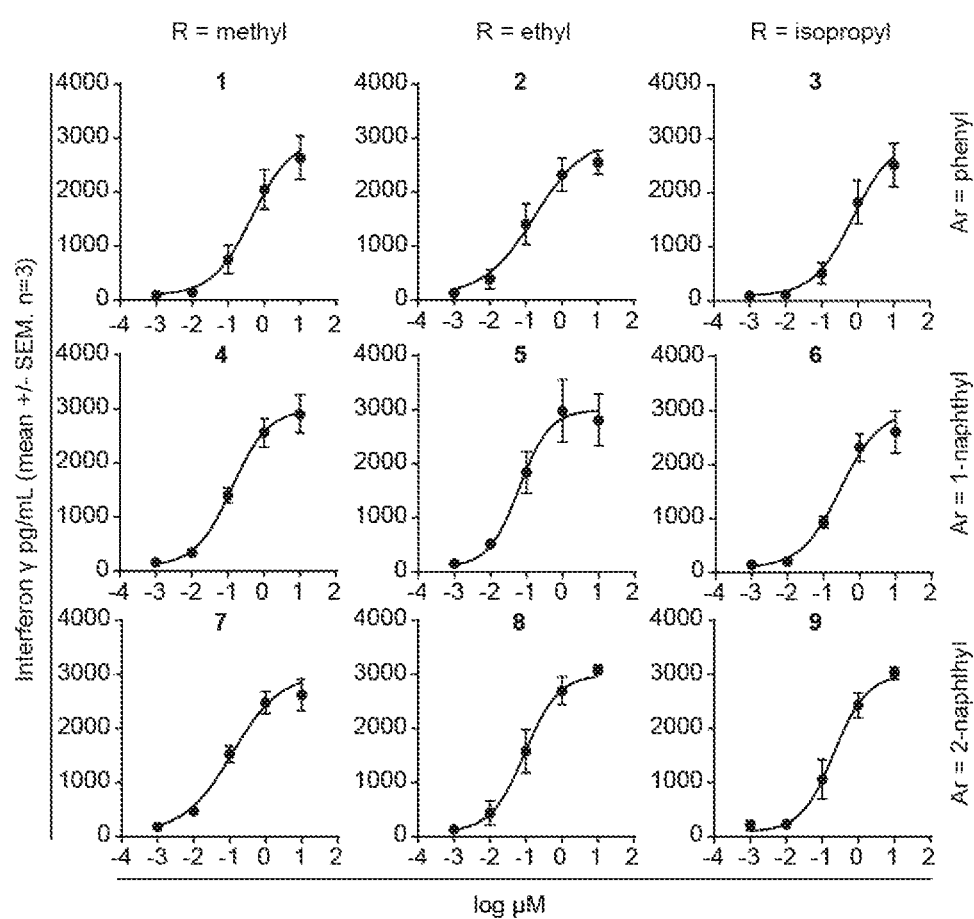
FIG. 4. K562 cells loaded with phosphonamidate prodrugs stimulate production of interferon γ by Vγ9Vδ2 T cells. Each compound was assessed in three independent experiments using a minimum of two different human donors.
Figure 5:
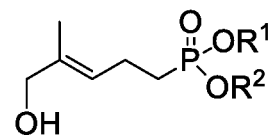
FIG. 5. A potent mixed aryl acyloxyalkyl butyrophilin ligand (103) and some control compounds.
Figure 5:
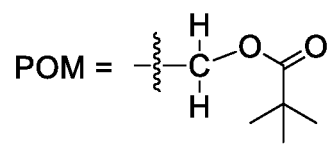

ELISA for interferon γ. Interferon γ was measured by ELISA as previously described and according to manufacturer's directions (see Kilcollins, A. M., et al., J. Immunol. 2016, 197, 419-428; and Shippy, R. R., et al., J Med. Chem. 2017, 60, 2373-2382. Briefly, K562 cells were treated with test compounds for 4 hours, washed, then mixed with V79Vδ2 T cells that had been purified by negative selection. Each well contained a 3:1 effector: target ratio in 200 μL. After 20 hours, the concentration of interferon γ in the supernatant was determined. Data for representative compounds of the invention is shown in Table 2 (see FIG. 4).

TABLE 2

Interferon γ production by Vγ9Vδ2 T cells in response
to K562 cells loaded for 4 hours with test compounds.

| Compound | $EC_{50}$ [μM] (95% CI) |
|---|---|
| 1 | 0.46 (0.29 to 0.71) |
| 2 | 0.17 (0.070 to 0.42) |
| 3 | 0.74 (0.42 to 1.3) |
| 4 | 0.13 (0.11 to 0.15) |
| 5 | 0.062 (0.037 to 0.11) |
| 6 | 0.29 (0.14 to 0.59) |
| 7 | 0.12 (0.056 to 0.26) |
| 8 | 0.093 (0.069 to 0.13) |
| 9 | 0.21 (0.15 to 0.30) |
| Mean Ar = phenyl | 0.46 |
| Mean Ar = 1-naphthyl | 0.16 |
| Mean Ar = 2-naphthyl | 0.14 |
| Mean R = methyl | 0.24 |
| Mean R = ethyl | 0.11 |
| Mean R = isopropyl | 0.41 |

Figure 3:
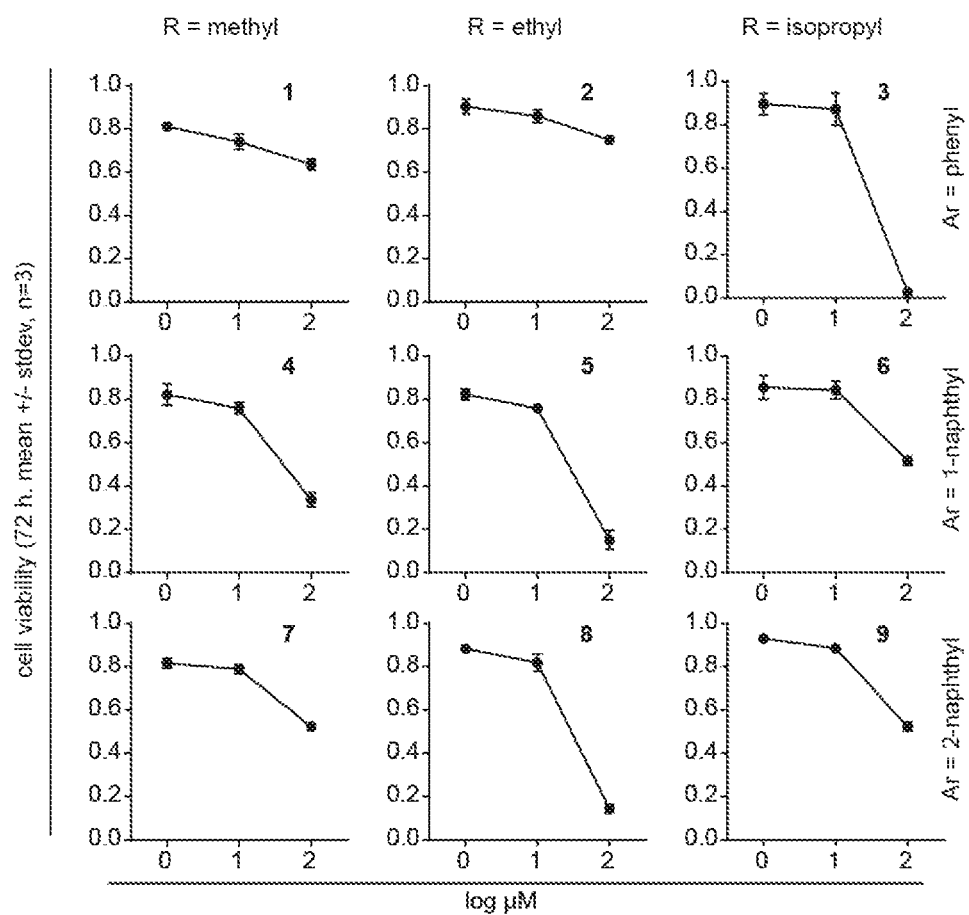
FIG. 3. K562 cell toxicity of phosphonamidate prodrugs. K562 cells were treated with test compounds for 72 hours and viability was assessed. Each compound was assessed in three independent experiments.

Cell viability. Viability assays were performed using K562 cells with various concentrations of test compounds. K562 cells (0.5×10$^4$ cells in 100 μL of RPMI media) were distributed into each well of a 96-well plate. Phosphonamidates were added for 72 hours, during the last 2 hours the cell-QB reagent was added, following which signals were quantified with a fluorescence plate reader. Viable cells were expressed as a percentage of untreated control cells after subtraction of a media-only blank. Data for representative compounds of the invention is shown in Table 3 (see FIG. 3).

TABLE 3

72 hour cytotoxicity of test compounds against K562 cells.

| Compound | $IC_{50}$ [μM] |
|---|---|
| 1 | >100 |
| 2 | >100 |
| 3 | 23 |
| 4 | 40 |
| 5 | 24 |
| 6 | >100 |
| 7 | >100 |
| 8 | 28 |
| 9 | >100 |
| Phenol | >100 |
| 1-naphthol | >100 |
| 2-naphthol | >100 |

Stability studies. Pooled human plasma was diluted to 50% with phosphate buffered saline at pH 7.5. Test compounds were added at a final concentration of 100 μM in a volume of 100 μL. Compounds were incubated for various times as indicated in the text, then extracted with 300 μL of LCMS grade acetonitrile and vigorous mixing. Insoluble debris was pelleted by centrifugation at 10,000 rcf for 2 minutes. 10 μL of the extract was evaluated by LCMS with a Waters Synapt G2-Si Mass Spectrometer in positive mode using a gradient of water and acetonitrile and a C18 column. The gradient started at 25% acetonitrile then increased to 80% acetonitrile over 9 minutes and held there for 1 minute before re-equilibration. The retention times for all compounds were as follows ($POM_2$-C-HMBP, $^tR$=5.43; 1, $^tR$=3.33; 2, $^tR$=3.72; 3, $^tR$=4.11; 4, $^tR$=4.16; 5, $^tR$=4.51; 6, $^tR$=4.87; 7, $^tR$=4.21; 8, $^tR$=4.55; 9, $^tR$=4.91 minutes). For all phosphonamidates tested, masses corresponding to the molecular ion [M+H]+, the sodium adduct [M+Na]$^+$, and the dehydration product [M-OH]$^+$ were observed at the reported retention time. The integrated values of these peaks were compared to those of t=0 minutes in plasma for each test compound and expressed as a fraction of the initial compound that was remaining at a given time point. Data for representative compounds of the invention is shown in Table 4 (see FIG. 1).

TABLE 4

Stability of compounds in 50% pooled human plasma in PBS.

| Compound | 2 hour fraction remaining (SD) | 24 hour fraction remaining (SD) | $t_{1/2}$ |
|---|---|---|---|
| 104 | 0.048 (0.034) | N.D. | 0.14 h |
| 1 | 0.97 (0.055) | 0.90 (0.11) | >24 h |
| 2 | 1.0 (0.042) | 0.96 (0.12) | >24 h |
| 3 | 0.99 (0.029) | 0.92 (0.050) | >24 h |
| 4 | 0.97 (0.035) | 0.76 (0.029) | >24 h |
| 5 | 1.0 (0.0071) | 0.89 (0.014) | >24 h |
| 6 | 1.0 (0.0071) | 0.95 (0.0071) | >24 h |
| 7 | 1.0 (0.0071) | 0.82 (0.0071) | >24 h |
| 8 | 1.0 (0.021) | 0.92 (0.035) | >24 h |
| 9 | 1.0 (0.085) | 0.95 (0.12) | >24 h |

Additional biological studies for compounds 2, 5, and 8 have been reported by Chia-Hung Christine Hsiao and Andrew J. Wiemer, *Biochemical Pharmacology*, 2018, 158, 298-304.

Example 13

The following illustrate representative pharmaceutical dosage forms, containing a compound of formula I or a pharmaceutically acceptable salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |

| (iii) Capsule | mg/capsule |
|---|---|
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

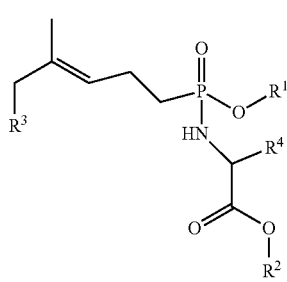

(I)

or a salt thereof, wherein:

$R^1$ is aryl, 5-6 membered heteroaryl, aryl($C_1$-$C_6$)alkyl, or (5-6 membered heteroaryl)($C_1$-$C_6$)alkyl, wherein any aryl, 5-6 membered heteroaryl, aryl($C_1$-$C_6$)alkyl, or (5-6 membered heteroaryl)($C_1$-$C_6$)alkyl is optionally substituted with one or more groups $R^x$ independently selected from the group consisting of hydroxyl, halo, nitro, cyano, carboxy, $NR^aR^b$, ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkylthio, and ($C_2$-$C_6$)alkanoyloxy, wherein any ($C_1$-$C_6$)alkyl and ($C_1$-$C_6$)alkoxy of $R^x$ is optionally substituted with one or more groups independently selected from halo;

$R^2$ is ($C_1$-$C_6$)alkyl that is optionally substituted with one or more groups independently selected from the group consisting of hydroxy, halo, nitro, cyano, carboxy, $NR^cR^d$, ($C_1$-$C_6$)alkoxy, ($C_1$-$C_6$)alkanoyl, ($C_1$-$C_6$)alkoxycarbonyl, ($C_1$-$C_6$)alkylthio, and ($C_2$-$C_6$)alkanoyloxy;

$R^3$ is oxo (=O) or hydroxy;

$R^4$ is the side-chain of a natural amino acid;

each $R^a$ and $R^b$ is independently selected from the group consisting of H, ($C_1$-$C_6$)alkyl, ($C_3$-$C_6$)cycloalkyl, and ($C_3$-$C_6$)cycloalkyl($C_1$-$C_6$)alkyl; or $R^a$ and $R^b$ together with the nitrogen to which they are attached form a aziridino, azetidino, morpholino, piperazino, pyrrolidino or piperidino, which aziridino, azetidino, morpholino, piperazino, pyrrolidino or piperidino is optionally substituted with one or more groups independently selected from the group consisting of halo and ($C_1$-$C_6$)alkyl; and each $R^c$ and $R^d$ is independently selected from the group consisting of H, ($C_1$-$C_6$)alkyl, ($C_3$-$C_6$)cycloalkyl, and ($C_3$-$C_6$)cycloalkyl($C_1$-$C_6$)alkyl; or $R^c$ and $R^d$ together with the nitrogen to which they are attached form a aziridino, azetidino, morpholino, piperazino, pyrrolidino or piperidino, which aziridino, azetidino, morpholino, piperazino, pyrrolidino or piperidino is optionally substituted with one or more groups independently selected from the group consisting of halo and ($C_1$-$C_6$)alkyl.

2. The compound of claim 1 or a salt thereof, wherein $R^1$ is aryl or aryl($C_1$-$C_6$)alkyl, wherein any aryl and aryl($C_1$-$C_6$)alkyl is optionally substituted with one or more groups $R^x$ independently selected from the group consisting of hydroxyl, halo, nitro, cyano, carboxy, $NR^aR^b$, ($C_1$-$C_6$)alkyl, ($C_1$-$C_6$)alkoxy, ($C_1$-$C_6$)alkanoyl, ($C_1$-$C_6$)alkoxycarbonyl, ($C_1$-$C_6$)alkylthio, and ($C_2$-$C_6$)alkanoyloxy, wherein any ($C_1$-$C_6$)alkyl and ($C_1$-$C_6$)alkoxy of $R^x$ is optionally substituted with one or more groups independently selected from halo.

3. The compound or salt of claim 1, which is a compound of formula (Ia):

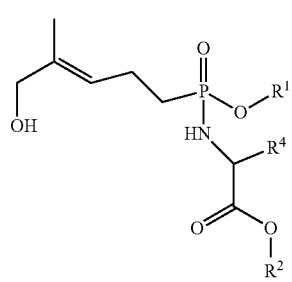

(Ia)

or a salt thereof.

4. The compound or salt of claim 1, which is a compound of formula (Ib):

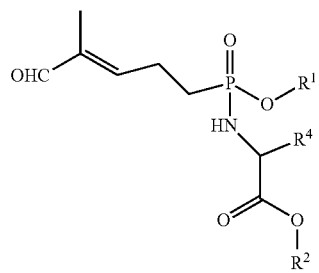

(Ib)

or a salt thereof.

5. The compound or salt of claim 1, wherein $R^1$ is phenyl that is optionally substituted with one or more groups $R^x$ independently selected from the group consisting of hydroxy, halo, nitro, cyano, carboxy, $NR^aR^b$, $(C_1-C_6)$alkyl, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy, wherein any $(C_1-C_6)$alkyl and $(C_1-C_6)$alkoxy of $R^x$ is optionally substituted with one or more groups independently selected from halo.

6. The compound or salt of claim 1, wherein $R^1$ is phenyl.

7. The compound or salt of claim 1, wherein $R^1$ is naphthyl that is optionally substituted with one or more groups $R^x$ independently selected from the group consisting of hydroxy, halo, nitro, cyano, carboxy, $NR^aR^b$, $(C_1-C_6)$alkyl, $(C_1-C_6)$alkoxy, $(C_1-C_6)$alkanoyl, $(C_1-C_6)$alkoxycarbonyl, $(C_1-C_6)$alkylthio, and $(C_2-C_6)$alkanoyloxy, wherein any $(C_1-C_6)$alkyl and $(C_1-C_6)$alkoxy of $R^x$ is optionally substituted with one or more groups independently selected from halo.

8. The compound or salt of claim 1, wherein $R^1$ is 1-naphthyl or 2-naphthyl.

9. The compound or salt of claim 1, wherein $R^2$ is $(C_1-C_6)$alkyl.

10. The compound or salt of claim 1, wherein $R^2$ is methyl, ethyl, or isopropyl.

11. The compound or salt of claim 1, wherein $R^4$ is H.

12. The compound or salt of claim 1, wherein $R^4$ is methyl.

13. A compound selected from:

1

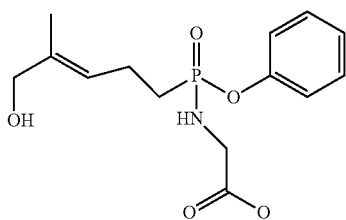

2

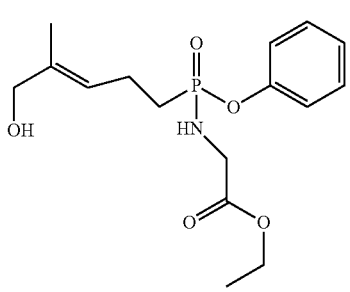

3

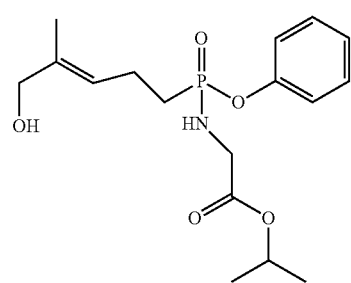

4

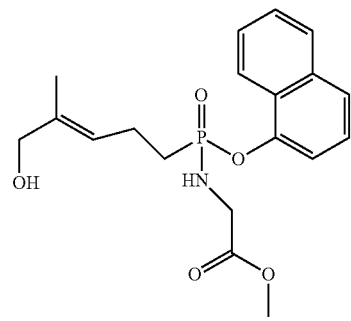

5

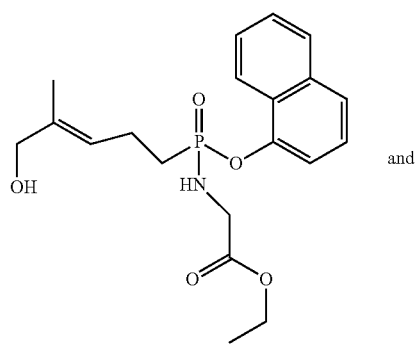

and

6

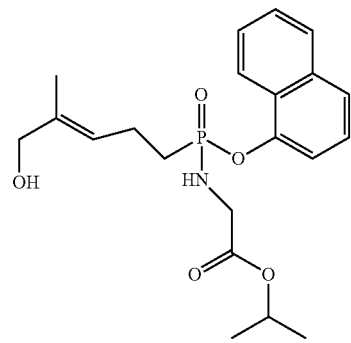

7

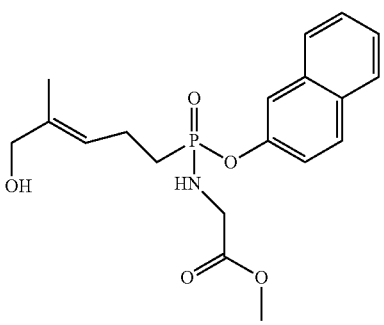

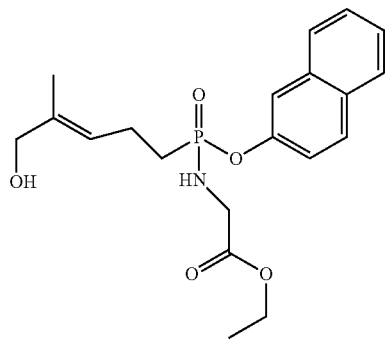

8

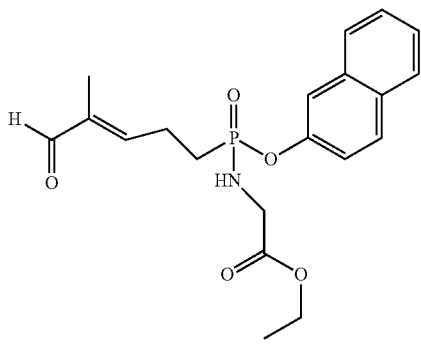

11 and

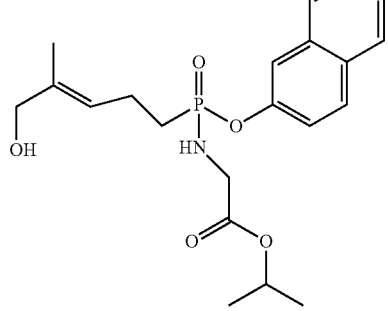

9

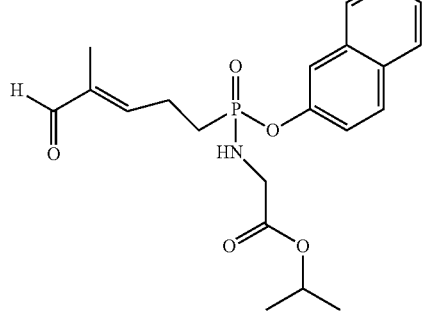

12

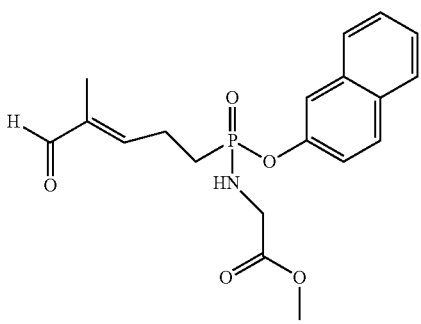

10 or a salt thereof.

14. A pharmaceutical composition comprising a compound as described in claim 1 or a pharmaceutically acceptable salt thereof and a pharmaceutically acceptable excipient.

15. A method for stimulating an immune response in an animal comprising administering a compound as described in claim 1, or a pharmaceutically acceptable salt thereof, to the animal.

16. A method for triggering the activation of gamma delta T cells in a human comprising administering a compound as described in claim 1, or a pharmaceutically acceptable salt thereof, to the human.

17. A method for triggering the activation or expansion of gamma delta T cells outside of a human comprising contacting the gamma delta T cells with a compound as described in claim 1, or a pharmaceutically acceptable salt thereof.

18. A method for stimulating an immune response in an animal comprising, administering a compound as described in claim 13 or a pharmaceutically acceptable salt thereof to the animal.

* * * * *